United States Patent [19]

Gordon et al.

[11] 4,190,064

[45] Feb. 26, 1980

[54] HAIR TREATMENT COMPOSITION AND METHOD OF TREATING HAIR WITH THE SAME

[75] Inventors: Harry W. Gordon, Bronx; Sharif Amanat, Elmshurst Queens, both of N.Y.

[73] Assignee: Del Laboratories, Inc., Farmingdale, N.Y.

[21] Appl. No.: 831,152

[22] Filed: Sep. 7, 1977

[51] Int. Cl.² ............................................. A45D 19/00
[52] U.S. Cl. .......................................... 132/7; 424/70
[58] Field of Search ............................... 132/7; 424/70

[56] References Cited

PUBLICATIONS

Hair–Dyes and Hair–Dyeing, Chemistry and Technique by H. Stanley Redgrove 1939, pp. 70 & 73.
Sagarin–Cosmetics–1957, pp. 491 and 493.

Primary Examiner—G.E. McNeil
Attorney, Agent, or Firm—Kirschstein, Kirschstein, Ottinger & Cobrin

[57] ABSTRACT

A hair treatment composition simultaneously tones, shampoos and conditions hair in from about one to about three minutes. The composition includes henna material having a natural lawsone component and a natural fixer component, an aqueous-based carrier having an acidic pH, a non-toxic organic solvent for extracting quantities of the natural lawsone and fixer components from the henna material, synthetic lawsone for making more coloring principle available, a fixing agent cooperating with the natural fixer component for fixing the natural lawsone component and/or synthetic lawsone to the hair, cleaning agents for shampooing the hair, and conditioning agents for conditioning the hair.

25 Claims, No Drawings

HAIR TREATMENT COMPOSITION AND METHOD OF TREATING HAIR WITH THE SAME

BACKGROUND OF THE INVENTION

1. Field of the Invention

The present invention generally relates to a hair treatment composition and, more particularly, to a method of treating hair by application of such composition to hair on the human head. Still more particularly, the present invention relates to a hair treatment composition which simultaneously tones, shampoos and conditions the hair to be treated in a short period of time.

2. Description of the Prior Art

Henna is a reddish-orange or reddish-brown vegetable dye made from the leaves of the shrub Lawsonia alba and related species such as Lawsonia inermis. The leaves contain about 1% of a coloring principle known as natural lawsone, as well as a natural fixer known as tannins, e.g., tannic acid.

In order to impart a reddish tone to the hair, it is known to dry such henna leaves and place them about the hair in compress or poultice form. The henna leaves then are covered with hot towels and kept warm with a casque heater until the desired degree of color is obtained.

It is also known to dry and to powder such henna leaves into particulate form. The dried powdered leaves then are steeped in boiling water and, while still warm, the ensuing henna solution is poured several times over freshly washed hair in order to tone the latter to the desired shade or tint.

Hair toning compositions in current use require a user to mix dried powdered henna leaves in very hot tap water until a paste or slurry is formed. This paste is applied to the hair and allowed to remain on the latter for approximately 45 minutes to about 2 hours for a suitable toning effect. Other recent hair toning compositions are marketed in creme form and similarly require lengthy application times for a suitable toning effect.

However, all of such known henna-type compositions have not proven to be altogether satisfactory. In use, only minimal degrees of toning or highlighting of the hair have been obtained. Moreover, the waiting times (generally on the order of 45 minutes to about 2 hours) required to process and tone the hair are too lengthy. Furthermore, subsequent washing or shampooing of the hair tends to wash out whatever toning effect has previously been imparted to the hair. Still furthermore, the known compositions do not adequately provide for any simultaneous conditioning of the hair.

It is further known to add ammonium lauryl sulfate, i.e., a detergent, to dried powdered henna leaves in order to form a combination toner and shampoo composition. However, the resulting toning effect imparted to the hair is unsatisfactory. It is believed that this unsatisfactory toning effect is due to the fact that the natural lawsone dissolves in a water carrier and forms a plurality of anions. The ammonium lauryl sulfate similarly dissolves in the water carrier to form a plurality of anions. It is believed that the negative ions of the ammonium lauryl sulfate actually tend to repel the negative ions of the lawsone, thereby resulting in a very minimal and highly unsatisfactory toning of the hair.

SUMMARY OF THE INVENTION

Accordingly, it is the general object of the present invention to overcome the aforementioned drawbacks of the prior art.

It is an additional object of the present invention to effectively and reliably tone and highlight hair to a desired reddish shade.

Still another object of the present invention is to tone and highlight hair to a reddish shade in very short processing times which are generally on the order of from 1 to about 3 minutes.

Another object of the present invention is to reliably fix the coloring principle lawsone to the hair such that subsequent shampooing will not tend to wash out the toning effect previously imparted to the hair.

Still another object of the present invention is to provide a combination shampoo and henna toner and conditioner composition for simultaneous application to the hair to be treated.

In keeping with these objects and others which will become apparent hereinafter, one feature of the invention resides, briefly stated, in a method of treating hair which includes the step of intermixing henna material, a non-toxic organic solvent, and an aqueous-based carrier having an acidic pH. Among other constituents, henna material contains a coloring principle (i.e., natural lawsone) and a natural fixer (i.e., tannins). The organic solvent extracts quantities of the natural lawsone and the natural fixer. Upon application of this mixture to hair to be treated, the natural fixer fixes the natural lawsone to the hair to thereby tone the same.

In order to make the hair treatment a more efficient procedure, synthetic lawsone is added to the mixture. Thus, additional quantities of coloring principle are available to assist the natural lawsone in imparting a reddish shade to the hair in a relatively shorter period of time.

Moreover, a fixer agent is added to the mixture and is operative for assisting the natural fixer in fixing the natural and/or synthetic lawsone to the hair in a short period of time.

In order to shampoo and condition the hair simultaneously with toning the same, cleaning and conditioning agents are added to the mixture.

The above-identified constituents of the hair treatment composition according to the present invention are present in amount and concentration sufficient to effectively and reliably tone the hair to the desired reddish shade in processing times generally on the order of one to three minutes. This represents a significant improvement over the rather lengthy processing times of the prior art. Moreover, we have found that the toning effect provided by our hair treatment composition does not tend to wash out with subsequent shampooings.

The novel features which are considered as characteristic for the invention are set forth in particular in the appended claims. The invention itself, however, together with additional objects and advantages thereof, will be best understood from the following description.

DESCRIPTION OF THE PREFERRED EMBODIMENTS

Hair is treated in accordance with the method of the present invention by applying a hair treatment composition to the hair. In the context of the present specification, the term "hair" is intended to include both natural human hair and synthetic hair which is part of a wig. The composition is comprised of a henna extract, i.e., concentrate, in amount from about 0.5% to about 20% by weight of the composition. The preferred amount of henna extract is from about 1% to about 5%, and the preferred value is about 2%.

The henna extract is obtained from henna material, such as dried henna leaves in whole or preferably in particulate form; an aqueous-based carrier, preferably deionized water; and a non-toxic organic solvent. The non-toxic organic solvent and the henna material are intermixed in the carrier at room temperature. The henna material has a natural coloring principle component, viz. lawsone, and a natural fixer component, viz. natural tannins such as tannic acid. When the henna material is mixed with the carrier and with the organic solvent, quantities of the natural lawsone component and of the natural fixer component are extracted from the henna material and are released to the carrier. The extraction process may be speeded up by heating the mixture of henna material, organic solvent and carrier to temperatures in the range from about 40° C. to about 70° C. A preferred temperature in this range is 60° C. Upon subsequent application of the resulting composition to the hair to be treated, the extracted natural fixer component fixes the extracted natural lawsone component to the hair to thereby tone or highlight the same.

Various types of non-toxic organic solvents such as monohydric alcohols (ethanol) and polyhydric alcohols (glycol) may be employed to extract the natural lawsone and natural fixer components from the henna material. In the glycol family, propylene glycol, butylene glycol, pentalene glycol, hexalene glycol and other glycols from C=7 to C=12 are particularly advantageous. Any polyethylene glycol having a molecular weight from 300 to 800 is preferred. Glycerins may also be employed.

We have preferred to use hexylene glycol because it has hydrophylic, humectant, and emollient characteristics which contribute to the conditioning of the hair. Hexylene glycol has the following structural formula:

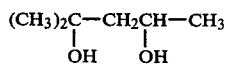

We have also used polyethylene glycol having a molecular weight of 400. In addition, we have successfully tested propylene glycol. The polyethylene glycol and propylene glycol are used in the same amounts as given below for hexylene glycol.

The henna extract preferably but not necessarily includes cleaning or detergent agents for shampooing the hair. Any cleaning agent may be employed; and N-Acetyl Ethanolamine, Cocamide Betaine, and Amphoteric-9 have been tested successfully as detergents in our composition. All of these detergents are operative for extracting additional quantities of natural lawsone and natural fixer components from the henna material. This feature makes more lawsone and more fixer available and thereby permits more rapid fixing of the lawsone to the hair. The structural formula for N-Acetyl Ethanolamine is:

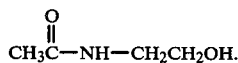

The structural formula for Cocamide Betaine is:

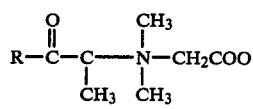

Where R is an alkyl radical such as lauryl, etc.
The structural formula for Amphoteric-9 is:

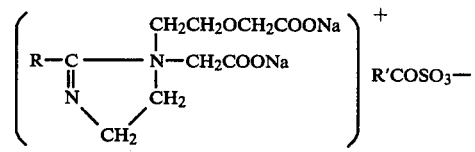

Where R is a coconut fatty radical such as lauryl, etc, and R' is a mixture of lauryl and laureth.

The henna extract preferably but not necessarily further includes preservatives and bacteria-fighting agents such as Methylparaben having the structural formula

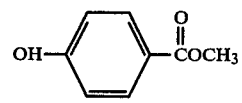

and/or Imidazolidinyl Urea having the structural formula:

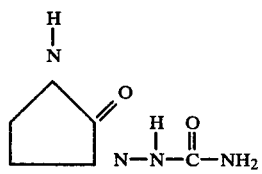

We have made henna extract from the following constituents in the following preferred ranges by weight:

| Constituents | Range (%) | Preferred Range (%) | Preferred Value (%) |
|---|---|---|---|
| Dried powdered Henna leaves | 1–60 | 10–40 | 15 |
| Hexylene Glycol (or polyethylene glycol or propylene glycol) | 5–40 | 15–30 | 25 |
| N-Acetyl Ethanolamine (or cocamide Betaine or Amphoteric-9) | 5–30 | 15–25 | 20 |
| Methylparaben | 0.1–0.3 | 0.1–0.3 | 0.15 |
| Imidazolidinyl urea | 0.1–0.5 | 0.1–0.5 | 0.2 |
| Deionized water | Balance | Balance | Balance |

The henna treatment composition further preferably but not necessarily comprises a fixing agent such as Adipic Acid/Dimethylaminohydroxy Propyl Diethylenetriamine which has the following structural formula:

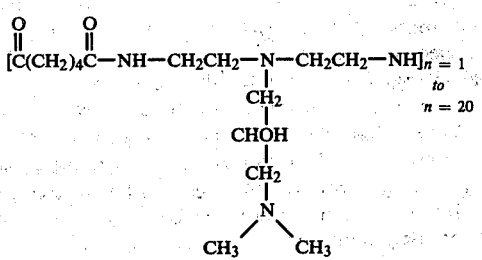

This fixing agent is a cationic polyamide-amine copolymer which is soluble in water and in certain blends of water and lower alcohols (e.g., ethyl alcohol). It is compatible with most anionic, nonionic, amphoteric and cationic surfactants over a broad pH range. This fixing agent is a clear yellow liquid and has a pH from about 8.0 to about 9.0. This fixing agent is operative in assisting the natural fixer component of the henna material in fixing the natural lawsone component to the hair in a more rapid time. The actual time in which fixing occurs depends, inter alia, upon the amount of fixing agent actually added to the composition. A preferred amount of this fixing agent is about 0.5–10% by weight of the composition; 2.0–6.0% being a preferred range; and about 4.0% being a preferred value.

The hair treatment composition still further preferably but not necessarily comprises synthetic lawsone or 2 Hydroxy 1, 4-Napthoquinone which has the following structural formula:

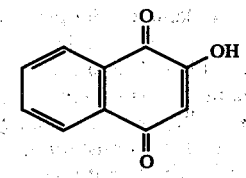

This synthetic coloring agent assists the natural lawsone component in adding more color or toning to the hair as compared to merely relying solely on the natural lawsone component. A preferred amount by weight of the composition of the synthetic lawsone is about 0.0–2.0%; 0.5% being the preferred approximate value.

The hair treatment composition yet further preferably but not necessarily comprises cleaning or detergent agents which assist the detergent agent already present in the henna extract in shampooing the hair. We have successfully employed Cocamido Betaine in amount by weight on the order of 0.0–40.0%; 10.0–30.0% being the preferred range; and 15.0% being the preferred value. The structural formula for Cocamido Betaine was given above.

In addition, we have added another detergent agent designated as Amphoteric-9. The structural formula for Amphoteric-9 was given above. Amphoteric-9 can be used as the sole cleaning agent, or Cocamido Betaine can be employed as the only cleaning agent. Currently, we prefer to employ both Amphoteric-9 and Cocamido Betaine simultaneously in the hair treatment composition.

This additional detergent agent preferably constitutes by weight of the composition in amounts from 0.0–50.0%; 10.0–40.0% being the preferred range; and 30.0% being the preferred value.

Amphoteric-9 and Cocamido Betaine both produce a plurality of cations when dissolved in a carrier having an acidic pH. The cations of such cationically-biased cleaning agents do not repel the negative ions of the natural lawsone component when the latter is dissolved in the carrier. This feature overcomes the prior art drawback of utilizing anion-biased detergents which disadvantageously influence the toning effect.

The hair treatment composition also includes preferably but not necessarily Polysorbate 20 in amounts from 0.0%–5.0% by weight. This makes the above-cited detergent agents much milder in their effect and helps to prevent tears from forming should the detergent agent inadvertently enter a user's eyes. Polysorbate 20 has the following structural formula:

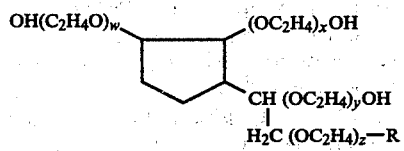

Where sum of w,x,y, and z is 20, and
R = $CH_3(CH_2)_{10}COO-$

The hair treatment composition in addition includes Lauramide DEA in amounts by weight of the composition from about 0.0%–5.0%. This is a foaming and thickening agent which contributes to proper shampoo consistency. The structural formula for Lauramide DEA (N-Lauryl Diethanolamine) is as follows:

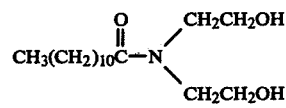

Also included in the hair treatment composition may be a conditioning agent for conditioning the hair. We have used a hydrolyzed animal protein in amounts by weight of the composition from about 0.0% to about 5.0%; 0.25% being the preferred value. The structural formula for the hydrolyzed animal protein is:

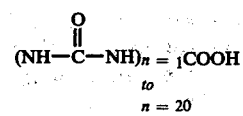

A preservative agent such as Disodium EDTA is also added to the composition and serves as a bacteria-fighter. The preferred range by weight of the composition of the preservative agent is 0.0–0.5% with 0.2% being the preferred value. The structural formula for this agent is:

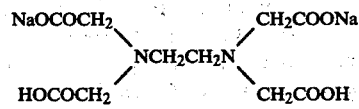

The pH of the hair treatment composition is preferably adjusted to an acidic level by adding an acidic agent to the composition prior to application to the hair. We have used citric acid in order to adjust the pH of the composition to a range from about 4.0 to about 6.5; 4.5-6.0 being the preferred pH range; and 5.5 being the preferred value for the entire hair treatment composition. The structural formula for citric acid is:

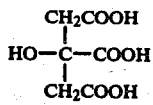

For aesthetic purposes only, FD&C Red No. 4 and/or D&C Red No. 33 may be added to the composition as desired. We have successfully used 0.06% by weight of the Red No. 4, and 0.001% by weight of the Red No. 33.

For aroma purposes only, perfume or fragrance be added to the composition in amounts by weight as is commercially desirable, usually on the order of 0.5% by weight of the composition. Deionized water makes up the balance of the composition.

A purely exemplary composition of a hair treatment shampoo with conditioner and toner has been fabricated with the following constituents and preferred percentages by weight of the overall composition:

| | |
|---|---|
| Amphoteric-9 | 30% |
| Adipic Acid/Dimethyl Aminohydroxypropyl Diethylenetriamine | 4% |
| Polysorbate 20 | 1% |
| Lauramide DEA | 1% |
| Cocamido Betaine | 15% |
| Synthetic Lawsone | 0.5% |
| Disodium EDTA | 0.2% |
| Hydrolyzed animal protein | 0.25% |
| Citric Acid | as desired to pH 5.5 |
| FD&C No. 4 | 0.06% |
| D&C No. 33 | 0.001% |
| Perfume | 0.5% |
| Henna Extract | 2% |

This purely exemplary hair treatment composition imparted color highlights or toning to the hair, cleaned the hair, and conditioned the hair in from about 1 to about 3 minutes. This represents a significant improvement in processing times as compared to the prior art compositions.

It will be understood that each of the elements described above, or two or more together, may also find a useful application in other types of applications differing from the types described above.

While the invention has been illustrated and described as embodied in hair treatment compositions and method of treating hair with the same, it is not intended to be limited to the details shown, since various modifications and constituent changes may be made without departing in any way from the spirit of the present invention.

Without further analysis, the foregoing will so fully reveal the gist of the present invention that others can by applying current knowledge readily adapt it for various applications without omitting features that, from the standpoint of prior art, fairly constitute essential characteristics of the generic or specific aspects of this invention and, therefore, such adaptations should and are intended to be comprehended within the meaning and range of equivalence of the following claims.

What is claimed as new and desired to be protected by Letters Patent is set forth in the appended claims:

1. A method of treating hair, comprising the steps of:
   (a) mixing henna material having a natural lawsone component and a natural fixer component in an aqueous-based carrier;
   (b) mixing a glycol with the henna material in the carrier and thereby extracting quantities of the natural lawsone and fixer components from the henna material to thereby form a henna extract;
   (c) mixing synthetic lawsone with the extract to thereby form a sub-mixture for increasing the color intensity imparted to the hair to a level above that imparted to the hair by the extracted natural lawsone component alone;
   (d) mixing a cationic polymeric fixing agent with the sub-mixture to thereby form a hair treatment composition for fixing both the synthetic lawsone and the extracted natural fixer component to the hair in a time period which is shorter than the time required for the extracted natural fixer component alone to fix the extracted natural lawsone component to the hair; and
   (e) applying the hair treatment composition to the hair for toning the same with the increased color intensity and in the shorter time period.

2. The method of claim 1, and further comprising the step of cleaning the hair simultaneously with said applying step by adding a cleaning agent to said composition prior to such application, said cleaning agent being operative for shampooing the hair and also for extracting additional quantities of said natural lawsone component and said natural fixer component from said henna material.

3. The method of claim 2, wherein said cleaning step includes adding a cation-biased cleaning agent.

4. The method of claim 1; and further comprising the step of conditioning the hair simultaneously with said applying step by adding a conditioning agent to said composition prior to such application.

5. The method of claim 1; and further comprising the step of adjusting the pH of said composition to an acidic level by adding an acidic agent to said composition prior to such application.

6. The method of claim 1, wherein said step of mixing a fixing agent includes mixing a cationic polyamide-amine copolymer with the sub-mixture.

7. The method of claim 1, wherein said step of mixing a cationic polyamide-amine copolymer with the sub-mixture includes mixing adipic acid/dimethylaminohydroxy propyl diethylenetriamine.

8. The method of claim 1, wherein said shorter time period is from about one to about three minutes.

9. The method of claim 1, wherein said step of mixing a glycol includes mixing hexylene glycol with the henna material in the carrier.

10. A method of making a hair treatment composition, comprising:
    (a) mixing henna material having a natural lawsone component and a natural fixer component in an aqueous-based carrier;
    (b) mixing a glycol with the henna material in the carrier and thereby extracting quantities of the natural lawsone and fixer components from the henna material to thereby form a henna extract;
    (c) mixing synthetic lawsone with the extract to thereby form a sub-mixture for increasing the color intensity imparted to the hair to a level above that imparted to the hair by the extracted natural lawsone component alone; and (d) mixing a cationic polymeric fixing agent with the sub-mixture to thereby form a hair treatment composition for fixing both the synthetic lawsone and the extracted natural fixer component to the hair in a time period which is shorter than the time required for the extracted natural fixer component alone to fix the extracted natural lawsone component to the hair.

11. The method of claim 10, wherein said step of mixing a fixing agent includes mixing a cationic polyamide-amine copolymer with the sub-mixture.

12. The method of claim 11, wherein said step of mixing a cationic polyamide-amine copolymer with the sub-mixture includes mixing adipicacid/dimethylaminohydroxy propyl diethylenetriamine.

13. The method of claim 10, wherein said shorter time period is from about one to about three minutes.

14. The method of claim 10, wherein said step of mixing a glycol includes mixing hexylene glycol with the henna material in the carrier.

15. The method of claim 10; and further comprising the step of mixing a cation-biased cleaning agent with the hair treatment composition.

16. The method of claim 10; and further comprising the step of mixing a conditioning agent with the hair treatment composition.

17. The method of claim 10; and further comprising the step of mixing an acidic agent with the hair treatment composition.

18. A hair treatment composition for application to hair, comprising:
(a) an aqueous-based carrier;
(b) henna material having a natural lawsone component and a natural fixer component in the carrier;
(c) a glycol in the carrier for extracting quantities of the natural lawsone and fixer components from the henna material to thereby form a henna extract;
(d) synthetic lawsone in the extract to thereby form a sub-mixture for increasing the color intensity imparted to the hair to a level above that imparted to the hair by the extracted natural lawsone component alone; and
(e) a cationic polymeric fixing agent in the sub-mixture to thereby form a hair treatment composition for fixing both the synthetic lawsone and the extracted natural fixer component to the hair in a time period which is shorter than the time required for the extracted natural fixer component alone to fix the extracted natural lawsone component to the hair.

19. The composition of claim 18, wherein said fixing agent is a cationic polyamide-amine copolymer.

20. The composition of claim 19, wherein said cationic polyamide-amine copolymer is adipic acid/dimethylaminohydroxy propyl diethylenetriamine.

21. The composition of claim 18, wherein said glycol is hexylene glycol.

22. The composition of claim 18; and further comprising a cation-biased cleaning agent in said carrier for cleaning the hair.

23. The composition of claim 18; and further comprising a conditioning agent in said carrier for conditioning the hair.

24. The composition of claim 18; and further comprising an acidic agent in said carrier for adjusting the pH of said composition to an acidic level.

25. A hair treatment composition, comprising:
(a) a henna extract comprising approximately 2% by weight of the composition, said extract including
  (i) dried powdered henna leaves comprising about 10% to about 40% by weight of the extract,
  (ii) hexylene glycol comprising about 15% to about 30% by weight of the extract,
  (iii) N-acetyl ethanolamine comprising about 15% to about 25% by weight of the extract,
  (iv) methylparaben comprising about 0.1% to about 0.3% by weight of the extract,
  (v) imidazolidinyl urea comprising about 0.1% to about 0.5% by weight of the extract,
  (vi) deionized water comprising the balance by weight of the extract;
(b) amphoteric-9 comprising about 30% by weight of the composition;
(c) adipic acid/dimethyl aminohydroxy propyl diethylenetriamine comprising about 4% by weight of the composition;
(d) polysorbate 20 comprising about 1% by weight of the composition;
(e) lauramide diethanolamine comprising about 1% by weight of the composition;
(f) cocamido betaine comprising about 15% by weight of the composition;
(g) synthetic lawsone comprising about 0.5% by weight of the composition;
(h) disodium ethylene diamine tetra acetate comprising about 0.2% by weight of the composition;
(i) hydrolyzed animal protein comprising about 0.25% by weight of the composition;
(j) citric acid comprising a percentage as desired to pH 5.5;
(k) FD&C red No. 4 comprising about 0.06% by weight of the composition;
(l) D&C red No. 33 comprising about 0.001% by weight of the composition; and
(m) perfume comprising about 0.5% by weight of the composition.

* * * * *